United States Patent [19]

Cignarella et al.

[11] Patent Number: 4,692,447
[45] Date of Patent: Sep. 8, 1987

[54] TRICYCLIC DIHYDROPYRIDAZINONES AND PHARMACEUTICAL COMPOSITIONS CONTAINING THEM

[75] Inventors: Giorgio Cignarella; Carmelo A. Gandolfi; Odoardo Tofanetti; Piervitto Cipolla; Sergio Tognella, all of Milan, Italy

[73] Assignee: Boehringer Biochemia Robin, S.p.A., Milan, Italy

[21] Appl. No.: 757,429

[22] Filed: Jul. 22, 1985

[30] Foreign Application Priority Data

Jul. 27, 1984 [GB] United Kingdom ............... 8419253

[51] Int. Cl.$^4$ ............... C07D 237/36; A61K 31/50
[52] U.S. Cl. ............... 514/248; 544/234; 260/501.17; 562/462; 564/222; 568/328; 568/330
[58] Field of Search ............... 544/234; 514/248

[56] References Cited

U.S. PATENT DOCUMENTS

| | | | |
|---|---|---|---|
| 3,464,988 | 9/1969 | Holava et al. | 544/234 |
| 3,475,431 | 10/1969 | Bachmann et al. | 544/239 |
| 4,602,019 | 7/1986 | Sircar et al. | 544/234 |

FOREIGN PATENT DOCUMENTS 0124314 11/1984 European Pat. Off.
0169443 1/1986 European Pat. Off.

OTHER PUBLICATIONS

Curran et al., *J. Med. Chem.*, vol. 17, No. 3, pp. 273-281, (1974).
Holava et al., *J. Med. Chem.*, vol. 14, No. 3, pp. 262-264.
Yamada et al., *J. Med. Chem.*, vol. 25, pp. 975-982, (1982).
Mukherjee et al., *J. Ind. Chem. Soc.*, vol. 58(10), pp. 1023-1024, (1981).
Dalton et al., *Aust. J. Chem.*, vol. 25, pp. 625-632, (1972).
Cignarella et al., *Il Farmaco-Ed. Sc.*, vol. 37, No. 2, pp. 133-144, (1981).
Cignarella et al., *Farmaco Ed. Sc.*, vol. 33, No. 11, pp. 866-874, (1978).
Loriga et al., *Farmaco Ed. Sc.*, vol. 34, No. 1, pp. 72-80, (1979).
Davies et al., *J. Chem. Soc.*, C, (2), pp. 327-329, (1970).

*Primary Examiner*—Donald G. Daus
*Assistant Examiner*—Emily Bernhardt
*Attorney, Agent, or Firm*—Murray and Whisenhunt

[57] ABSTRACT

The tricyclic dihydropyridazinone derivatives having formula I

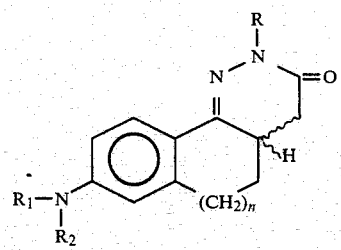

are endowed with interesting hypotensive, vasodilating, antiaggregant, antithrombotic and cytoprotective properties and are therefore useful in human or veterinary medicine.

7 Claims, No Drawings

TRICYCLIC DIHYDROPYRIDAZINONES AND PHARMACEUTICAL COMPOSITIONS CONTAINING THEM

The present invention relates to tricyclic dihydropyridazinones, to a process for their preparation and to pharmaceutical and veterinary composition containing them.

The compounds of the invention have the general formula I

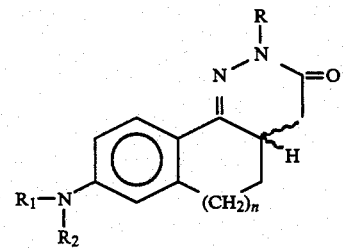

wherein
n is zero or an integer from 1 to 2;
R is a member selected from the group consisting of hydrogen, a $C_1$–$C_6$ lower alkyl, —$CH_2$—CH=$CH_2$, $CH_2$—C≡CH and

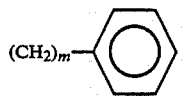

being m zero or an integer from 1 to 3;
$R_1$ and $R_2$ are independently selected from the group consisting of hydrogen, a $C_1$–$C_6$ lower alkyl,

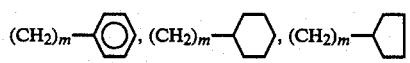

wherein m is as above defined, $CH_2$—CH=$CH_2$, —$CH_2$—C≡CH, $R_3$—CO— or $R_4SO_2$— where $R_3CO$ is the acyl part of a carboxylic acid $R_3CO_2H$ selected from the group consisting of: a $C_1$–$C_{16}$ unbranched and branched aliphatic fatty acid and derivatives thereof containing hydroxy, amino halogen, or thiol groups such as formic, acetic, propionic, butyric, isobutyric, stearic, lactic, cystein, alanine, leucine, valine, thioglycolic, glycolic, ε-aminocapronic, chloroacetic, 2-chloropropionic; an aromatic acid such as benzoic o,m,p-toluic; 3,4,5-trimethoxybenzoic, p-hydroxy-3,5-dimethoxy-benzoic, p-fluoro-benzoic, p-chloro-benzoic, p-aminobenzoic, salicylic, p-hydroxybenzoic;
an heterocyclic acid such as nicotinic acid, isonicotinic, pyrazol-3 carboxylic acid, isoxazol-3-carboxylic and 5-carboxylic, 2-thiophencarboxylic, 2-furylcarboxylic;
a $C_4$–$C_8$ cycloaliphatic acid such as cyclopropylcarboxylic, cyclopentane carboxylic, cyclohexane carboxylic acid;
a $C_5$–$C_{16}$ cycloaliphatic alkyl, aralkyl, heteroalkyl acid such as cyclopentyl acetic, cyclopentyl propionic, cyclopentoxyacetic, cyclohexyl propionic, phenoxyacetic, phenyl propionic, 1-imidazolylacetic, 2-furylpropionic, 2-tetrahydrofuryl propionic, cinnamic, 2-fluoro-cinnamic, caffeic acid;
a dicarboxylic fatty acid such as oxalic, succinic, glutaric, fumaric having the other carboxylic group free or salified or esterified with a lower $C_1$–$C_6$ alkyl;
a carbonic acid wherein $R_3$ is a lower $C_1$–$C_6$ alkoxy, benzyloxy or $NHR_c$ where $R_c$ is hydrogen, a $C_1$–$C_6$ lower alkyl, or benzyl;
$R_4SO_2$ is the sulphonyl part of a sulphonic acid preferably selected from the group consisting of methanesulphonic, ethanesulphonic, benzenesulphonic, p-toluensulphonic and canfosulphonic.

The compounds of formula I having n=o are referred to as: 4,4a-dihydro-5H-indeno-[1,2-c]-pyridazin-3-one and the amino substituent in the ring A is a 7-amino substituent.

The compounds of formula I having n=1 are referred to as: 4,4a,5,6-tetrahydro-2H-benzoin)-cinnolin-3-one and the amino substituent in the ring A is an 8-amino-substituent.

The compounds of formula I having n=2 compounds are referred to as 2,4,4a,5,6,7-hexahydro-3H-benzo-[6,7]cyclohepten-[1,2-c]-pyridazin-3-one and the amino substituent in the ring A is a 9-amino-substituent.

The present invention refers also to the non toxic salts, for pharmaceutical suitable or veterinary use, as well as the optical antipodes, i.e. the enantiomers, the racemic mixtures of the optical antipodes and the mixtures of the diasteroisomers of the compounds of formula (I).

In the formulae of this specification, when the absolute configuration of the CH bond at the junction of the rings B/C is defined, the heavy solid line ◂ indicates that a substituent at the junction of the ring B/C is in the β-configuration, i.e. above the plane formed by the ring A/B (exo-configuration); the dotted lines ( . . . . ) indicates that a substituent at the junction of the ring B/C in the α-configuration, i.e. below the plane formed by the ring A/B (endo configuration).

The wavy line bond ( ⸾ ) indicates that the stereochemistry of the substituent at the junction of the ring B/C is not defined as in the case of racemic mixture of the compounds of formula I.

When R, $R_1$, $R_2$ are achiral substituents, the compounds of the formula I are a 1:1 mixture of the compounds of the following formulae:

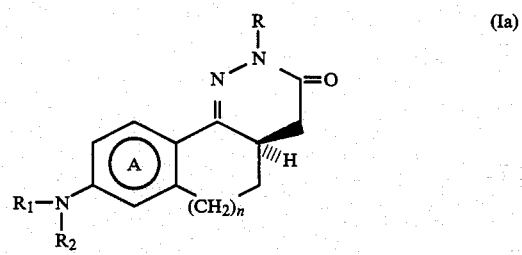

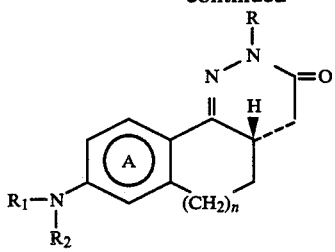
(Ib)

Consequently when R, R$_1$, R$_2$ are chiral substituents the compounds of the invention are mixtures of racemic diasteroisomers which are also included in the scope of the present invention.

Specific examples of preferred compounds of the invention are:
4,4a-dihydro-5H-indeno[1,2-c]pyridazin-3-one-7-amino;
4,4a-dihydro-5H-indeno[1,2-c]pyridazin-3-one-7-formamide;
4,4a-dihydro-5H-indeno[1,2-c]pyridazin-3-one-7-acetamide;
4,4a-dihydro-5H-indeno[1,2-c]pyridazin-3-one-7-benzamide;
4,4a-dihydro-5H-indeno[1,2-c]pyridazin-3-one-7-(3',4',5'-trimethoxy)-benzamide;
4,4a-dihydro-5H-indeno[1,2-c]pyridazin-3-one-7-nicotinyl-amide;
4,4a,5,6-tetrahydro-2H-benzo(h)cinnolin-3-one-8-amino;
4,4a,5,6-tetrahydro-2H-benzo(h)cinnolin-3-one-8-acetamide;
4,4a,5,6-tetrahydro-2H-benzo(h)-cinnolin-3-one-8-2'-chloroacetamide;
2-n-butyl-4,4a,5,6-tetrahydro-2H-benzo(h)cinnolin-3-one-8-amino;
2-n-butyl-2,4,4a,5,6,7-hexahydro-3H-[6,7]-cyclohepten-[1,2-c]-pyridazin-3-one-8-amino;
2-n-butyl-2,4,4a,5,6,7-hexahydro-3H-[6,7]-cyclohepten-[1,2-c]-pyridazin-3-one-8-benzamide;
2,4,4a,5,6,7-hexahydro-3H-benzo-[6,7]-cyclohepten-[1,2-c]-pyridazin-3-one-8-amino;
2,4,4a,5,6,7 -hexahydro-3H-benzo-[6,7]-cyclohepten[1,2-c]-pyridazin-3-one-8-acetamide;
2,4,4a,5,6,7-hexahydro-3H-benzo-[6,7]-cyclohepten[1,2-c]-pyridazin-3-one-8-benzamide;
and the single optical antipodes.

The compounds of the invention are prepared by a process comprising the reaction of a racemic and/or optically active compound of the general formula II

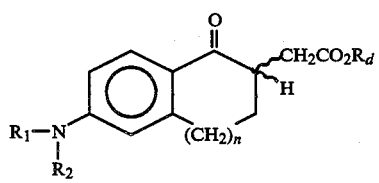
(II)

wherein n, R$_1$ and R$_2$ are as above defined and R$_d$ is a member selected in the group consisting of hydrogen and C$_1$-C$_6$ lower alkyl with a hydrazine compound of formula III

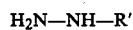
H$_2$N—NH—R' (III)

wherein R' is a member selected in the group consisting of hydrogen, lower C$_1$-C$_6$ alkyl, phenyl to give a compound of the general formula Ia

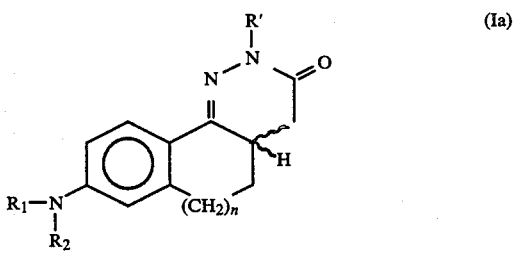
(Ia)

wherein n, R$_1$, R$_2$, and R' are as above defined.

The compounds of formula Ia, wherein either R$_1$ or R$_2$, is hydrogen and the other one is a C$_1$-C$_6$ lower alkyl,

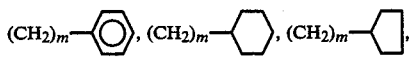

—CH$_2$—C=CH$_2$ or —CH≡CH, may be optionally reacted with a convenient activated form of a carboxylic acid of formula R$_3$CO$_2$H and/or with a convenient activated form of a sulphonic acid of formula R$_4$SO$_3$H wherein R$_3$ and R$_4$ have the above defined meanings.

The compounds of formula Ia wherein both R$_1$ and R$_2$ are hydrogen, are optionally alkylated so as to obtain a compound wherein either R$_1$ or R$_2$ is hydrogen and the other one is a C$_1$-C$_6$ lower alkyl, a group of formula

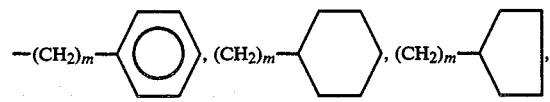

CH$_2$=CH—CH$_2$ or HC≡C=CH; the, the alkylated compounds can be optionally acylated by an activated acid of formula R$_3$CO$_2$H or R$_4$SO$_3$H.

The compounds of formula Ia wherein R' is hydrogen can be optionally transformed into the compounds wherein R' has the other above defined meanings by reaction with an halocompound such as lower C$_1$-C$_6$ alkyl-X, XCH$_2$—CH=CH$_2$, X—CH$_2$—C≡CH,

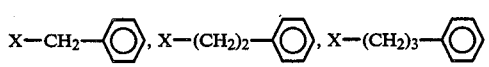

wherein X may be Cl, Br or I and is preferably iodine, in the presence of a base.

Said alkylation reaction may also be optionally carried out on compounds wherein R' is hydrogen and either R$_1$ or R$_2$ are hydrogen and the other one is a group of formula R$_3$—CO or R$_4$SO$_2$, obtaining thereby the double-alkylated products of formula I wherein R and either R$_1$ or R$_2$ are a C$_1$-C$_6$ lower alkyl, allyl, propargyl, or a group of formula

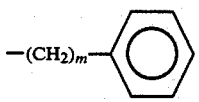

wherein m is 1, 2 or 3.

In the process for the preparation of the compounds of the present invention, the final compounds of the invention are racemic substances if the starting material of general formula II is a racemic substance.

In this case, the compounds of formula Ia or I may be optionally submitted to optical resolution to their optical antipodes. Therefore, for example, the compounds of formula Ia wherein $R_1$ and $R_2$ are independely hydrogen, $C_1$–$C_6$ lower alkyl, —$CH_2$—$CH$=$CH_2$, —$CH_2$—$C$≡$CH$,

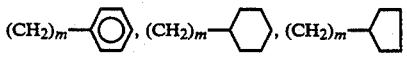

may be submitted to optical resolution by crystallization of the salts with optically active acids such as, for example, d-tartaric, l-tartaric, l- and d-dibenzoyltartaric acid, d- and l-canfosulphonic acid, d- and l-6-exochloro-7-sincarboxy-bicyclo[2,2,1]-heptan-3-one-3,3-ethylenedioxy, d- and l-mandelic acid, d- and l-malic. Otherwise, for example, when one of $R_1$ and $R_2$ is a $R_3CO$ acyl substituent wherein $R_3$ is an ω-free carboxylic group such as $HO_2C$—$(CH_2)_q$— wherein q is zero or an integer from 1 to 6 or a group of formula

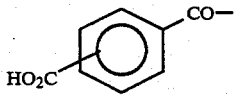

The optional optical resolution may be carried out by fractional crystallization of the salts with optical active bases such as for example d- and l-ephedrine; d- and l-α-phenylethylamine, dihydroabiethylamine and so on.

On the other hand, for example when in the compounds of formula Ia or I one of $R_1$ and $R_2$ is a $R_3CO$-acyl substituent comprising an ω-free basic group such as $NH_2$—$(CH_2)_q$—$CO$ (q=1–6) or

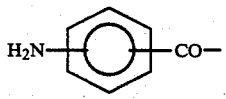

or a basic heterocyclic group such as, for example,

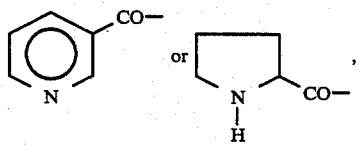

the optional optical resolution may be performed by crystallization of the salts with the above optically active acids. In addition to these conventional methods, if it is desired, the optional optical resolution may be performed by chromatographic separation on optically active phases.

Preferably, the optional optical resolution is carried out on the racemic compounds of formula Ia, i.e. after the reaction of a racemic compound of formula II with a hydrazine compound of formula III, taking into account the racemizations due to enolization of the ketogroup of the optically active compounds of formula II.

The reaction of a compound of formula II with a hydrazine compound of formula III can be carried out in a solvent selected in the group consisting of $C_1$–$C_4$ alcohols, glycols, such as ethylene glycol, propylenglycol; ethers such as dimethoxy ethane, dioxane, tetrahydrofuran; water; formic and acetic acids, and mixtures thereof using equimolecolar amounts and/or an excess of the hydrazine compounds and/or salts thereof which are soluble in the solvents at temperatures ranging from the room temperature to the boiling point of the mixture, for reaction times from a few minutes to twentyfour hours.

The preferred solvent is ethanol, the preferred temperature is the reflux temperature for a time of 30 minutes.

The optional acylation of a compound of the general formula Ia where either $R_1$ or $R_2$ are hydrogen, may be carried out in the presence of a inorganic and/or organic base in an inert solvent such as dichloromethane, 1,2-dichloroethane, benzene, toluene, chlorobenzene, dimethoxyethane, tetrahydrofuran, dimethylformamide, dimethylsulphoxyde, pyridine, dimethylaniline, N,N-diethylacetamide with known activated forms of carboxylic acid $R_3$—$CO_2H$ or a sulphonic acid $R_4$—$SO_3H$.

The preferred activated forms are the acid chlorides, anhydrides and their mixed anhydrides.

The inorganic bases are alkali and alkali-earth bicarbonates and carbonates.

The organic bases are selected in the group consisting of tertiary amines such as triethylamine, tributylamine, pyridine, collidine, dimethylaniline, diethylaniline. The reaction can be carried out using equimolecolar amounts and/or an excess of the acylating reagent at temperatures ranging from zero to the solvent reflux temperature. The room temperature is preferably used.

The optional alkylation of a compound of general formula Ia is carried out with methods known in the art: for example a preferred method is the reductive amination by reaction with an aldehyde and/or ketone and $NaCNBH_3$. The alkylamino derivative so obtained, if desired, can then be acylated as above described.

The optional alkylation of the dihydropyridazinone ring wherein R' is hydrogen, is carried out by reacting the compound with a suitable halocompound in an inert solvent such as acetone, dimethylformamide, dimethylsulfoxide, dimethoxyethane, tetrahydrofuran, benzene, diethylacetamide and their mixtures in the presence of a base such as potassium hydroxyde, potassium ter-butoxyde, potassium carbonate, $CH_3SOCH_2Na$, $CH_3SOCH_2K$, sodium hydride, diisopropyldithioamide. The reaction temperature is from −60° to 80° C., the time from few minutes to twenty-four hours using equimolecolar amounts of the reagents and/or an excess thereof.

The compounds of the general formula II are unknown compounds; and, therefore, they also are object of the invention.

Compounds II are obtained by a multistep process reacting a compound of the general formula IV

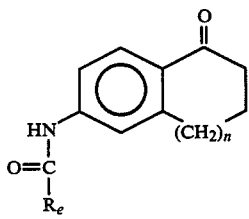

wherein n is as above defined and $R_e$ is selected among lower $C_1$-$C_3$ alkyl, preferably methyl; $CF_3$, phenyl, benzyloxy; with "in situ" formed glyoxylic acid or an ester thereof to give an alkylidene compound of the general formula V

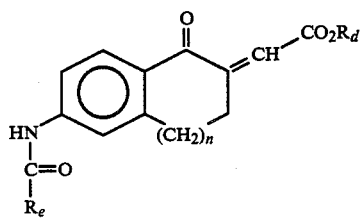

wherein $R_e$, $R_d$, n are as above defined.

Compound V is then reduced to give a compound of general formula VI

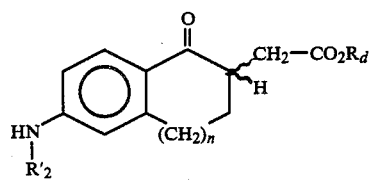

wherein $R_d$ is as above defined and $R'_2$ is a member selected in the group of hydrogen, lower acyl, preferably acetyl, trifluoroacetyl, benzoyl, benzyloxy carbonyl, which is then optionally hydrolyzed and hence, using methods known in the art, the obtained free amino group is optionally converted into a substituted amino group for example by reductive alkylation with aliphatic, aromatic, heterocyclic aralkyl, heteroalkyl aldehydes and ketones; the obtained compounds are optionally submitted to acylation with an activated form of the $R_3CO_2H$ and $R_4SO_3H$ acids and these compounds are optionally submitted to optical resolution, in their racemic or optically active forms.

The glyoxylic acid ester are known substances, which may be formed "in situ" by treating tartaric acid and tartaric acid esters with an alkaline periodate in acidic medium.

The reaction of the compound of formula IV with a glyoxylic acid derivative (free acid or ester) is made in a water-miscible solvent such as lower alkyl alcohols, and preferably the same alcohol esterifying the glyoxylic acid, dimethoxyethane, tetrahydrofuran, dioxane and mixture thereof in the presence of a basic catalyst such as alkaline hydroxydes, alkaline bicarbonates and carbonates aqueous solutions, and/or in the presence of strong organic bases such as Triton A, tetrabutylammonium hydroxyde, piperidine, morpholine, pyrrolidine.

The reaction is preferably carried out at temperatures ranging from $-5°$ to about the reflux temperature, preferably the reaction is performed at room temperature.

The reaction times range from few minutes to several days, but usually do not exceed eight hours and three hours are often sufficient to complete the reaction.

The reduction of the double bond of the compounds of formula V is simply carried out by reaction in aqueous acetic acid with zinc dust, heating the mixture at temperature from 80° C. to 100° C. for a time of 30 minutes.

Otherwise, the reduction can be carried out by catalytic hydrogenation at room temperature and pressure in the presence of an Adam's platinum and/or palladium on charcoal, particularly when the acylating group of the aminogroup is a benzyloxycarbonyl, so obtaining at the same time reduction of exocyclic double bond and removal of the protective group of the amino group.

The removal of the acyl protective group of the amino group is carried out by refluxing a solution of the compound of formula VI wherein $R'_2$ is a lower acyl, trifluoroacetyl, benzoyl with a concentrated mineral acid solution, such as HCl, HBr or $6N$ $H_2SO_4$, for few minutes; the free amine is recovered after alkaline work-up.

The optional optical resolution of the compounds of formula VI may be performed both starting from the amino compounds of formula VI ($R'_2$=hydrogen, lower alkyl) and from the carboxylic acids of formula VI ($R_d$=hydrogen) using known methods and, respectively, known optically active acids and amines.

The compounds of the general formula IV are also obtained by a multistep process starting from known compounds.

When in the compounds of formula IV, n is zero, the starting material used in the process is the indane.

When in the compounds of formula IV n is the integer 1, the starting material is 1,2,3,4-tetrahydro-naphthalene.

When in the compounds of formula IV n is the integer 2, the starting material is benzo-cycloheptane.

Therefore starting materials for the compounds of formula V are bicyclic substances of the general formula VII

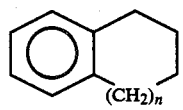

wherein n is as above defined. The process for the synthesis of the compounds of formula IV from the compounds of formula VII comprise the following steps:
(a) Friedel-Crafts reaction with an acylchloride of the general formula VIII, $R''_2$-COCl wherein $R''_2$ is a $C_2$-$C_4$ lower alkyl or phenyl to give a ketone of the general formula IX

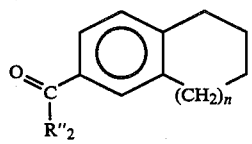

wherein n and $R''_2$ are as above defined;

(b) Beckmann rearrangement of the oximes of the ketones of formula IX and/or optionally Schmidt reaction by treatment of the same ketones with a hydrazoic acid solution to afford the amides of the general formula (X)

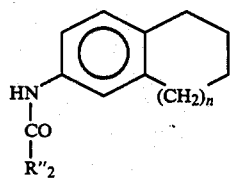

(X)

wherein R″$_2$ and n are as above defined;

(c) benzylic oxidation to give the ketones of the general formula XI

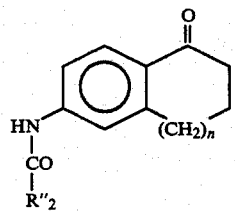

(XI)

whose acylamino group, if desired, is hence hydrolyzed and then optionally reacted with trifluoroacetic anhydride or benzyloxycarbonylchloride, so obtaining a compound of the general formula IV.

The above reactions are well-known in the art and they do not require further comments.

Because the benzocycloheptane, i.e. the compound of formula I where n is the integer 2, is not always easily available, the corresponding compounds of formula IV can be also prepared starting from 5-oxo-5-phenyl-pentanoic acid. This compound, as it is well known in the art, is obtained in Friedel-Craft conditions from benzene and glutaric anhydride.

The method described in the following Scheme 1 can be also useful for the preparation of the compounds of formula IV wherein n is the integer 1, starting from 4-oxo-4-phenyl-butanoic acid, available from benzene and succinic anhydride in Friedel-Craft conditions, too.

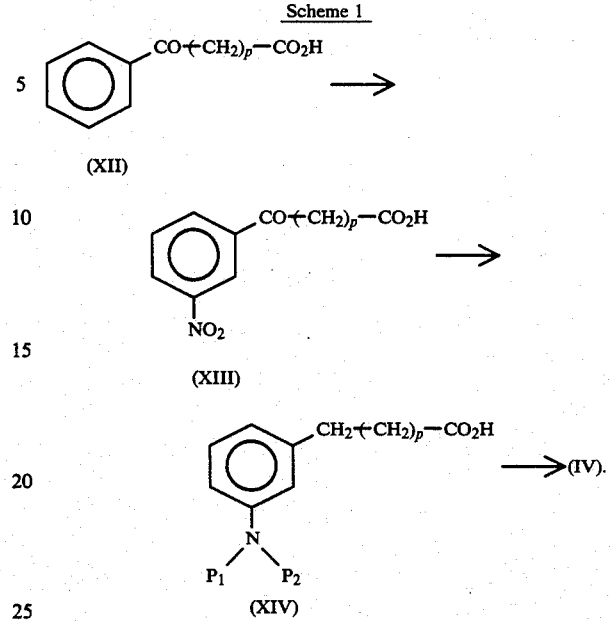

A ω-keto-ω-phenyl-alkanoic compound of formula XII wherein p is an integer from 1 to 2 is converted in the corresponding m-nitro-compound XIII, and then submitted to contemporaneous catalytic reduction of the keto and nitro groups affording the m-amino-phenyl-ω-alkanoic acid of formula XIV wherein P$_1$ and P$_2$ are hydrogen.

The reduction can be optionally performed in the presence of an anhydride and/or mixed anhydride so obtaining an acylamino compound of formula XIV where one of P$_1$, P$_2$ is hydrogen and the other one is an acyl residue.

Alternatively, if desired, the acylation reaction may be performed at the end of the catalytic reduction so obtaining an acylamino compound of formula XIV wherein one of P$_1$, P$_2$ is hydrogen and the other one is a member selected in the group of lower C$_2$–C$_4$ acyl, preferably acetyl, trifluoroacetyl; benzoyl, benzyloxy carbonyl, which is submitted to cyclization for example in polyphosphoric acid to yield the compound of formula IV.

According to the Scheme 2, and using substantially the same principle, the compounds of formula IV wherein R$_e$ is methyl and n is zero can be also obtained starting from known bromobenzyl compounds of formula XVI a, b and converted after elongation of the alkyl chain with malonic esters (XVIIa, b, R$_f$=lower alkyl) to the m-acetylaminophenyl-3-propanoic acid which is cyclized with polyphosphoric acid yielding the 5-acetylamino-indan-3-one.

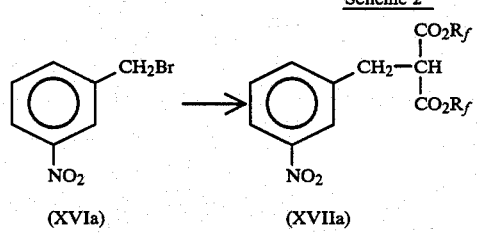

Scheme 2

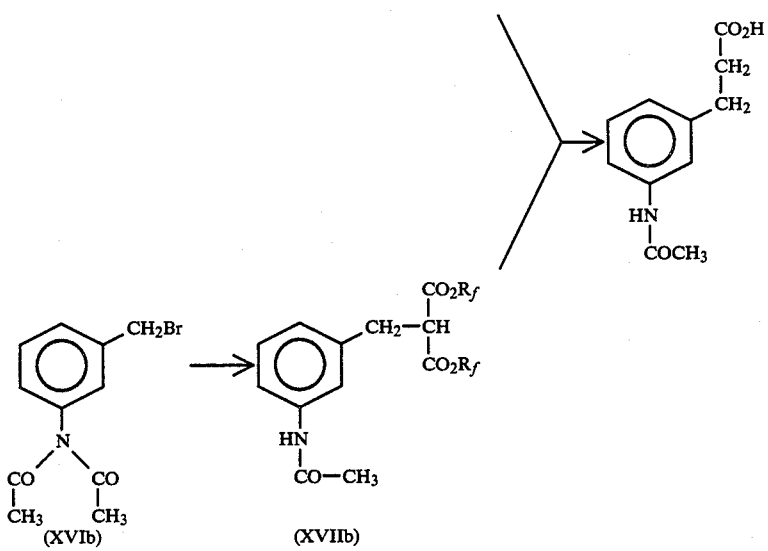

The above processes use reaction conditions well-known in the art, such as alkylation of malonic esters, hydrolysis followed by decarboxylation and the final cyclization with polyphosphoric acid as catalyst.

On the other hand, m-nitrobenzoic acid may be transformed by treatment with carbonyldiimidazole in the corresponding imidazolyde which is reacted with magnesium ethoxyde-monomalonic ethylester to give m-nitrobenzoyl acetic acid ethyl ester.

This compound can be then hydrogenated to give a compound of formula XIV wherein p is the integer 1; subsequent cyclization, for example using poliphosphoric acid, yields the compounds of general formula IV wherein n is zero.

The compounds of this invention can be used, in general, as cardiovascular protective agents in either human or veterinary medicine.

First of all, the compounds of the present invention are characterized by a low acute toxicity and a very favourable therapeutic index.

The Table 1 shows, for example, the results of experiments of acute toxicity in mice obtained with some of the representative compounds of the invention, such as:

BBR-1507  dl-7-acetylamino-4,4a-dihydro-5H-indeno-[1,2-c]pyridazin-3-one;
BBR-1508  dl-8-acetylamino-4,4a,5,6-tetrahydro-2H-benzo(h)-cinnolin-3-one;
BBR-1509 dl-8-acetylamino-2,4,4a,5,6,7-hexahydro-3H-benzo[6,7]-cyclohepten[1,2-c]-pyridazin-3-one;
BBR-1510 dl-8-amino-4,4a,5,6-tetrahydro-2H-benzo(h)-cinnolin-3-one;
BBR-1511  dl-1-n-butyl-8-amino-4,4a,5,6-tetrahydro-2H-benzo(h)cinnolin-3-one;
BBR-1512  dl-7-amino-4,4a-dihydro-5H-indeno[1,2-c]-pyridazin-3-one;
BBR-1513  dl-9-amino-2,4,4a,5,6,7-hexahydro-3H-benzo-[6,7]-cyclohepten[1,2-c]-pyridazin-3-one;
BBR-1514 dl-8-chloroacetylamino-4,4a,5,6-tetrahydro-2H-benzo(h)-cinnolin-3-one.

The compounds were administered by oral and intraperitoneal route.

TABLE 1

| Compound | $LD_{50}$ in mg/kg os | $LD_{50}$ in mg/kg i.p. | Compound | $LD_{50}$ mg/kg os | $LD_{50}$ mg/kg i.p. |
|---|---|---|---|---|---|
| BBR-1507 | >1000 | 310 | BBR-1511 | >1000 | 1000 |
| BBR-1508 | >1000 | 360 | BBR-1512 | 400 | 200 |
| BBR-1509 | >1000 | >1000 | BBR-1513 | 700 | 483 |
| BBR-1510 | >1000 | 610 | BBR-1514 | >1000 | >1000 |

All these compounds have a high anti-aggregating activity.

Using platelet-rich plasma (PRP) from guinea pigs and monitoring platelet aggrtegation by continuous recording of light trasmission in a Born aggregometer [Born G. V. R. Nature (London) 194, 927 (1962)] there is evidence that the compounds of the invention inhibit "in vitro" platelet aggregation.

The compounds from BBR-1507 to BBR-1514 were incubated for 10 minutes at 37° C. in the PRP prior to the addition of the aggregating agents ADP (0.5 μM), collagen (8 μg/ml),trombine (0.625 U/ml) and showed total inhibition when tested at concentrations from 5 to 15 μg/ml.

The same compounds from BBR-1507 to BBR-1513, given orally, protected against sudden death induced by arachidonate in mice. At the screening dosage of 20 mg/kg, the compounds BBR-1509, BBR-1511 and BBR-1513 were equiactive as acetylsalicylic acid (ASA) dosed at 200 mg/kg.

The compounds BBR-1507, 1510, 1512 showed a 20–30% increase of protection as compared with ASA; a 40% increase was evident when the tested compound was BBR-1508.

Sudden death (SD), a leading cause of human mortality, can strictly be defined as acute cardiac failure, associated with ventricular fibrillation. Its etiology is much complicated, and can involve vasospasm, thromboembolism, atherosclerosis and arrhytmias. Thromboxane $A_2$ is considered a mediator in SD due to its vasoconstrictive, platelet aggregating and arrythmic actions [see A. K. Myers, and P. W. Ramwell, Thromboxane and Sudden death. Proceed. Platelets Prostaglandins and cardiovascular system, pag. 22, Florence, Feb. 8–11 (1984)].

The compounds of the invention are, therefore, useful in mammals for inhibiting platelet aggregation, for preventing and inhibiting thrombus formation and for decreasing the adhesiveness of platelets.

Therefore, they are useful in treatment and prevention of thromboses and myocardial infarct, in treatment of atherosclerosis as well as in treatment of geriatric patients for prevention of cerebral ischemic episodes, and in long-term treatment after myocardial infarct.

This is particularly the case of compounds like as BBR-1511, 1513 and 1509 which show only a little (5–8 mmHg) even if prolonged hypotensive effect when tested in conscious normal and in spontaneously hypertensive rats at doses ranging from 100 to 200 mg/kg by intraperitoneal route.

The compounds BBR-1507, 1508 and BBR-1510, on the contrary, show a more evident and prolonged hypotensive effect when administered by intraperitoneal and oral route in conscious normotensive and in spontaneously hypertensive rats.

As it is shown in Table 2, the decrease of the systolic median blood pressure was long lasting and the length of the effect was dose-related.

TABLE 2

| Compound | Dose mg/kg | SHR Rats i.p. ΔBP sist | hr | SHR Rats os ΔBP sist | hr | Normotensive rats os ΔBP sist | hr |
|---|---|---|---|---|---|---|---|
| BBR-1507 | 50 | −55 | >4 | | | | |
| | 12.5 | n.t. | | −58 | 5.6 | −26 | 3 |
| | 6.25 | n.t. | | −50 | >4 | −8 | 3 |
| | 3.125 | n.t. | | −25 | 3 | n.t. | |
| | 1.56 | n.t. | | −18 | 1.5 | n.t. | |
| BBR-1508 | 25 | −90 | 3 | −65 | 4.6 | −48 | 4 |
| | 12.5 | −50 | 3 | −55 | 4.6 | −20 | 4 |
| | 6.25 | n.t. | | −30 | 4 | −8 | 1.5 |
| | 3.125 | n.t. | | −30 | 2 | inactive | |
| BBR-1510 | 12.5 | −80 | >4 | −60 | >3 | −28 | >6 |
| | 6.25 | −55 | 1 | −40 | 3.4 | n.t. | |
| | 3.125 | n.t. | | −46 | 2 | n.t. | |
| | 1.56 | | | −48 | 1 | n.t. | |

Because of their hypotensive and vasodilatatory activity, the compounds of the invention are useful for treatment of hypertensive diseases such as essential hypertension and in particular in hypertensive manifestations associated with platelet hyperaggregability.

The cytoprotective ability is a common feature of all the compounds. In a range of dosage from 20 to 100 mg/kg they displayed good potency in preventing gastric damage induced by ethanol and by ASA.

Said cytoprotective effect was particularly surprising because some of the tested compounds such as BBR-1507, 1508 and BBR-1510, in particular, were also effective in reducing the paw edema induced by carrageenin. The compounds were tested by oral route at three dose levels: 20, 60 and 200 mg/kg and they were slightly more active (1.5–2 times) than ASA.

The compounds BBR-1509 and BBR-1514 were inactive whereas the compound BBR-1513 was scarcely effective in reducing paw edema even if all these substances were at least equiactive as ASA in inhibiting platelet aggregation in "in vivo" and "in vitro" experiments (see above).

These experimental evidences allow to argue that the inhibition of the cyclooxygenase enzymes is not the preferred mechanism of action for the compounds of the present invention.

Their biological profile, including hypotensive and vasodilatory activity, "in vitro" and "in vivo" antiaggregating activity andcytoprotective activity is fairly indicating a prostacyclin-mimetic action.

The compounds of the invention are therefore also so useful in disturbance of the peripheral circulation tion and, therefore, in the prevention and treatment of diseases such as phlebitis, hepato-renal syndrome, non-obstructive mesenteric ischemia, arthritis and ischemic ulceration of the leg.

The compounds can be administered by the oral, intravenous, subcutaneous, intramuscular, rectal routes.

In emergency situations, the intravenous administrations is preferred.

The dose can vary from 0.5 to 100 mg/kg/day depending on the patient's condition, weight, age and on the administration route.

As previously stated, the compounds of the invention can be administered either to humans or animals in a variety of dosage forms, e.g., orally in the form of tablets, capsules or liquids; rectally, in the form of suppositories; parenterally, subcutaneously or intramuscularly, with intravenous administration being preferred in emergency situations; in the form of sterile implants for prolonged action. The pharmaceutical or veterinary compositions containing the compounds of the invention may be prepared in conventional ways and contain conventional carriers and/or diluents.

For example, for intravenous injection or infusion, sterile aqueous isotonic solutions are preferred. For subcutaneous or intramuscular injection, sterile solutions or suspensions in aqueous or non-aqueous media may be used; for tissue implants, a sterile tablet or silicone rubber capsule containing or impregnated with the compound is used.

Conventional carriers or diluents are, for example, water, gelatine, lactose, dextrose, saccharose, mannitol, sorbitol, cellulose, talc, stearic acid, calcium or magnesium stearate, glycol, starch, arabic gum, tragacanth gum, alginic acid or alginates, lecithin, polysorbate, vegetable oils, etc.

The invention is illustrated by the following non-limitative examples.

EXAMPLE 1

A solution of 90% hydrazine hydrate (0.26 ml) is added to a solution of dl-[1-oxo-5-amino-indan-2-yl]acetic acid (1 g) in ethanol (20 ml).

The mixture is heated at the reflux temperature for 2 hrs. After cooling at room temperature, the crystalline precipitate is filtered to yield 0.87 g of dl-7-amino-4,4a-dihydro-5H-indeno[1,2-c]-pyridazin-3-one, m.p. 235° C. (dec.).

I.R. 3200, 3280, 1650 cm$^{-1}$
H-NMR (DMSO/TMS) 10.4 (s, 1H, N=NH); 6.4–7.4 (m, 3H, Ar); 5.6 (s, 2H, NH$_2$); 2.4–3.6 (m, 5H, CH$_2$—CH-CH$_2$) p.p.m.

EXAMPLE 2

A solution of n-butylhydrazine acetate in ethanol (15 ml), prepared from n-butylhydrazine hydrochloride (1 g) and potassium acetate (0.82 g) is added to a solution in ethanol (15 ml) of dl-6-amino-1-oxo-1,2,3,4-tetrahydro-naphth-2-yl-acetic acid ethyl ester (0.9 g). The mixture is heated at 60° for 3 hrs, the excess of ethanol is evaporated in the vacuum and the residue is partitioned between ethyl acetate and 5% aqueous K$_2$HPO$_4$. The organic phases are collected, washed until neutral, dried on Na$_2$SO$_4$ and evaporated to dryness.

The residue is crystallized from methanol to give dl-1-n-butyl-8-amino-4,4a,5,6-tetrahydro-2H-benzo(h)-cinnolin-3-one, m.p. 140°–142° C.

IR : 3450, 3330, 1670 cm$^{-1}$
H-NMR (CDCl/TMS) =8 (d, 1H); 6.6 (d, 2H); 3.7–3.9 (m); 2.1–2.9 (m), 1.8 (m).

EXAMPLE 3

A solution of dl-8-amino-4,4a,5,6-tetrahydro-2H-benzo(h)-cinnolin-3-one (3 g) and n-butyl-bromide (5.7 g) in acetone (75 ml) is heated at reflux temperature in the presence of fine powdered potassium carbonate (5 g). The mixture is filtered, the acetone is evaporated and the residue is partitioned between water and ethyl acetate. The usual work-up affords a crude compound (3.9 g) which is crystallized from methanol to yield dl-1-n-butyl-8-amino-4,4a,5,6-tetrahydro-2H-benzo(h)-cinnolin-3-one m.p. 141°–142° C.

In similar way, starting from 7-amino-indenopyridazin-3-ones and 9-amino-benzocycloheptenpyridazin-3-ones the following compounds are obtained: dl-1-n-butyl-7-amino-4,4a-dihydro-5H-indeno[1,2-c]-pyridazin-3-one;
dl-1-n-butyl-7-acetylamino-4,4a-dihydro-5H-indeno-[1,2-c]-pyridazin-3-one;
dl-1-n-butyl-9-amino-2,4,4a,5,6,7-hexahydro-3H-benzo[6,7]-cyclohepten[1,2-c]-pyridazin-3-one, m.p. 97°–98° C.;
dl-1-n-butyl-9-acetylamino-2,4,4a,5,6,7-hexahydro-3H-benzo[6,7]-cyclohepten[1,2-c]-pyridazin-3- one.

EXAMPLE 4

A solution of hydrazine acetate in ethanol (20 ml) is prepared by mixing hydrazine hydrochloride (1.05 g) and potassium acetate (2 g) and added to a solution of 5-acetylamino-1-oxo-indan-2-yl acetic acid (2 g) in ethanol. The mixture is refluxed for 1.5 hours and then cooled at 0°–5° C. for 2 hours. The crystalline precipitate is filtered out affording 1.85 g of dl-7-acetyl-amino-4,4a-dihydro-5H-indeno[1,2-c]-pyridazin-3-one m.p. 315° C.

I.R. 3200, 1700, 1650 cm$^{-1}$; H-NMR (DMSO/TMS) =10.8 (s, 1H); 10.1 (s, 1H); 7.4–7.8 (m, 3H, Ar); 2.4–3.3 (m, 5H); 2 (s, 3H, CH$_3$CO).

EXAMPLE 5

A solution of dl-6-acetylamino-1-oxo-1,2,3,4-tetrahydro-naphth-2-yl-acetic acid (3.27 g) in ethanol (60 ml) was treated with 90% hydrazine hydrate (1 ml) and heated at the reflux temperature for 3 hrs. After cooling at 0°–5° C., the precipitate is separated by filtration and recrystallized from acetone-ethanol to yield 8-acetylamino-4,4a,5,6-tetrahydro-2H-benzo(h)-cinnolin-3-one m.p. 284° C.

I.R. 3100, 1700, 1650 cm$^{-1}$; H-NMR (DMSO/TMS) =11.4 (s, 1H); 10.4 (s, 1H); 7.8–8.5 (m, 3H, Ar).

A suspension of this compound (2.55 g) in 4N HCl (38 ml) is heated at the reflux temperature until a complete solution is obtained. After 2.5 hours, the mixture is cooled at room temperature, extracted with ethyl acetate to remove unreacted material. The aqueous phase is basified to pH 8.5, extracted with ethyl acetate to afford, after the usual work-up, 8-amino-4,4a,5,6-tetrahydro-2H-benzo(h)-cinnolin-3-one m.p. 277° C.

I.R. 3180, 3130, 1670 cm$^{-1}$.
H-NMR (DMSO/TMS): 10.8 (s, H); 7.8–6.3 (m, 3H, Ar); 5.5 (br.s, 2H, NH$_2$).

EXAMPLE 6

Using in the procedure of the Example 5 the dl-7-acetylamino-1-oxo-benzocycloheptan-2-yl-acetic acid, the following dihydropyridazinones are obtained:
dl-9-acetylamino-2,4,4a,(,6,7-hexahydro-3H-benzo-[6,7]-cyclohepten[1,2-c]-pyridazin-3-one m.p. 253–256° C. (from EtOH); IR =3200, 1700, 1650 cm$^{-1}$. DMSO-d$_6$/TMS: 10.6 (s, 1H); 9.9 (s, 1H); 7.2 (m, 3H, Ar); 1.8 (s, 3H, CHHD 3CO).

dl-9-Amino-2,4,4a,5,6,7-hexahydro-3H-benzo[6,7]-cyclohepten[1,2-c]-pyridazin-3-one m.p. 212°–214° C; I.R. =3420, 3340, 3200, 1700 cm$^{-1}$. DMSO-d$_6$/TMS: 10.8 (s, 1H); 6.4–7.4 (m, 3H, Ar); 5.3 (s, 2H, NH$_2$).

EXAMPLE 7

A solution of dl-7-amino-4,4a-dihydro-5H-indeno-[/1,2-c]-pyridazin-3-one (1.1 g) in toluene (25 ml) is treated with triethylamine (0.65 g) and chloroacetyl-chloride (0.735 g) and stirred for 6 hours at 50° C. After cooling, the mixture is partitioned with water, dried on Na$_2$SO$_4$ and evaporated to dryness. The residue is crystallized from DMF-water affording 1.05 g of dl-7-α-chloroacetylamino-4,4a-dihydro-5H-indeno [1,2-c]-pyridazin-3-one m.p. 200° C.

I.R. =3200, 1725, 1640, 1550 cm$^{-1}$.
H-NMR (DMSO/TMS): 10.8 (s, 1H); 7.5–8 (m, 3H, Ar); 4.4 (s, 2H, CHHD 2Cl).

Potassium thioacetate (0.4 g) is added to a solution of this compound (0.5 g) in DMF (8 ml) and the mixture is stirred for 4 hours at room temperature and then diluted with water (25 ml). The precipitate is collected by filtration and crystallized from acetone affording 0.42 g of dl-7-acetylthioacetylamino-4,4a-dihydro-5H-indeno[1,2-c/-pyridazin-3-one. I.R. =3200, 1720, 1641, 1550, 1230 cm$^{-1}$. H-NMR : 10.8 (s, 1H); 10.1 (s, 2H); 7.4–7.8 (m, 3H, Ar); 4.2 (s, 2H); 2 (s, 3H, CH$_3$-CO).

EXAMPLE 8

Using in the procedure of the Example 7 the α-chloro-propionyl-chloride and benzensulphonylchloride, the following compounds are prepared:
7-α-chloropropionylamino-4,4a-dihydro-5H-indeno -[1,2-c]-pyridazin-3-one, m.p. 250° C.;
7-benzensulphonylamino-4,4a-dihydro-5H-indeno[1,2-c]-pyridazin-3-one.

EXAMPLE 9

Anhydrous aluminum trichloride (25 g) is added dropwise to a stirred mixture of acetylchloride (11.8 g), indane (24 g) and dry benzene (100 ml) stirred at 5–8° C.

The stirring is continued for 6 hours at this temperature until the evolution of hydrogen chloride is over; then, the mixture is partitioned with ice (200 g) and 6N hydrochloric acid (100 ml), the organic phase is separated, the aqueous phase is extracted with benzene. The organic benzene layers are collected, washed until neutral, dried on MgSO$_4$ and the excess solvent is evaporated under vacuum. The residue (28.5 g) is distilled in high vacuum (1 mmHg) and the fractions with b.p. 80°–85° C. are collected affording 16 g of 5-acetylindane. I.R.=1680 cm$^{-1}$. H-NMR (CDCl$_3$/TMS): 7.1–7.8 (m, 3H, Ar); 2.9 (t, 4H); 2.55 (s, 3H, CH$_3$); 1.9–2.4 (m, 2H). A solution of 5-acetylindane (15 g) in ethanol (50 ml) is treated with a solution of hydroxylamine hydrochloride (15 g) and potassium acetate (21.5 g) in ethanol (50 ml) for 20 minutes at the reflux temperature. The excess of the solvent is evaporated in vacuum and the mixture is diluted with water. The precipitate is collected by filtration affording 15.01 g of 5-acetylindane oxime m.p. 104° C. I.R.=3200 cm$^{-1}$. H-NMR (CDCl$_3$/TMS): 8.15 (s, 1H, N—OH); 2.3 (s, 3H, CH$_3$).

A solution of 13.8 g of the above oxime in pyridine (140 ml) cooled at 0°–2° C. is treated under stirring with benzensulphonyl chloride (18 ml). The stirring is continued for 3 hours, then the mixture is poured in ice (0.7 kg) and 6N HCl (450 ml).

The precipitate is collected, dried under vaduum and crystallized from aqueous ethanol to yield 5-acetylaminoindane (11.2 g), m.p. 61° C. I.R. 3250, 1660 cm$^{-1}$. H-NMR (CDCl$_3$/TMS); 7.6–7.9 (m, 1H, NH); 7.1–7.5 (m, 3H, Ar).

The acetylaminoindane (11 g) is dissolved in glacial acetic acid (30 ml) added with acetic anhydride (8.4 ml), and then a solution of chromic anhydride (8.4 g) in acetic acid (14.7 ml) and water (3.7 ml) is added dropwise, under stirring and cooling to 5°–10° C. The mixture is furtherly stirred for 12 hours at room temperature, then treated with aqueous solution of sodium bisulphite to destroy the excess of oxidizing reagent and poured in ice-water (1:1; 250 g). The crystalline precipitete is collected by filtration to give, after crystallization from ethanol, 7.8 g of 5-acetylaminoindane-1-one m.p. 168° C.

I.R. 3250, 1690 cm$-1$. H-NMR (CDCl$_3$/TMS): 8.05 (s, 1H, NH); 7.2–7.8 (m, 3H, Ar); 2.5–3.3 (m, 4H, CHHD 2-CHHD 2); 2.2 (s, 3H, CH$_2$—CO).

Glyoxylic acid is prepared "in situ" by addition of a cooled solution of tartaric acid (8 g) in water (20 ml) to a stirred solution of periodic acid in water (75 ml) from NaIO$_4$ 11.3 g) and H$_2$SO$_4$ (1.3 ml), cooled to 0°–2° C.

5-Acetylamino-indan-1-one (5 g) in ethanol (75 ml) and 2.75 N aqueous NaOH (86.5 ml) are then added to this mixture maintaining the temperature of the reaction mixture at about 20°–24° C. The stirring is continued for 15 hours and the precipitate is removed by filtration. The eluate is acidified with 2N H$_3$SO$_4$ to crystallize the 5-acetylamino-1-oxo-indan-2-yliden-acetic acid (2.5 g), m.p. 255°–258° C. H-NMR (DMSO-d$_6$/TMS): 10.7 (s, 1H, NH); 6.4–6.8 (m, 1H,

2 (s, 3H, CHHD 3CO—).

Zinc dust (1.65 g) is added in portion to a solution of the inden-2-ylacetic acid (2.25 g) in 80% aqueous acetic acid (25 ml), heated at 100° C.; the stirring is continued for 45 minutes. The inorganic material is removed by filtration and washed with warm 80% aqueous acetic acid (25 ml). The eluates are collected and the excess of acetic acid is removed in vacuum. The residual aqueous phase is extracted with ethylether, yielding, after the usual work-up, the 5-acetylamino-1-oxo-indan-2-yl-acetic acid (1.65 g) m.p. 178°–180° C.

I.R.=3330, 1690, 1550 cm$^{-1}$; H-NMR (DMSO/TMS); 6.3–8.3 (m, 4H, Ar and NH); 3.15 (t, 2H, CH$_2$); 2.75 (t, 2H, CH$_2$); 2.2 (s, 3H, CH$_3$CO—).

A solution of this compound (0.5 g) in concentrated hydrochloric acid (2.5 ml) is heated at the reflux temperature for 20 minutes; the mixture is cooled to 10° C. and treated with 2N NaOH until pH 4.

The precipitate is filtered yielding 0.39 g of 5-amino-1-oxo-indan-2-yl-acetic acid m.p. 192°–194° C. I.R. 3300–3400, 1690 cm$^{-1}$.

EXAMPLE 10

Using 1,2,3,4-tetrahydro-naphthalene in the procedure of the Example 9 the following compounds are obtained:

6-acetyl-1,2,3,4-tetrahydro-naphthalene-oxime, m.p. 88°–90° C. 0,2 mmHg;

6-acetyl-1,2,3,4-tetrahydro-naphthalene-oxime, m.p. 104°–105° C. (EtOH);

6-acettyl-1,2,3,4-tetrahydro-naphthalene, m.p. 105–106° C. (aq. EtOH);

6-acetylamino-1-oxo-1,2,3,4-tetrahydronaphthalene, m.p. 123°–124° C.;

6-acetylamino-1-oxo-1,2,3,4-tetrahydro-naphth-2-yliden-acetic acid, m.p. 223°–225° C.;

6-acetylamino-1-oxo-1,2,3,4-tetrahydro-naphth-1-yl-acetic acid, m.p. 195°–197° C.;

6-amino-1-oxo-1,2,3,4-tetrahydro-naphth-1-yl-acetic acid.

EXAMPLE 11

A 1M HN$_3$ solution in chloroform (70 ml) is added to a solution of 6-acetyl-1,2,3,4-tetrahydronaphthalene(5 g) in chloroform (20 ml) and the mixture is treated with H$_2$SO$_4$ (d. 1.84, 2.5 ml), added dropwise under stirring for 40 minutes. After an additional stirring for 30 minutes at room temperture the reaction mixture is washed with water, 10% aqueous K$_2$HPO$_4$ and water, until the washings are neutral. The organic phase is dried on CaCl$_2$, the solvent is evaporated in vacuum to give 4.65 g of 6-acetylamino-1,2,3,4-tetrahydro-naphthalene m.p. 105.5°–106°. I.R.=3150, 1670 cm$^{-1}$. H-NMR 10.1 (s, 1H, NH); 7.1–8.0 (m, 3H , Ar); 1.7–3.1 (m+s, 11H).

In similar way, starting from 5-acetyl-indane, 5-acetylamino-indane, m.p. 62° C., is obtained.

EXAMPLE 12

4-Benzoylbutanoic acid (m.p. 124°–126° C.) is prepared by addition of a solution of glutaric anhydride (60 g) in benzene (140 ml) to a stirred suspension of aluminum trichloride (152 g) in benzene (200 ml), cooled at 5°–10° C. 4-Benzoylbutanoic acid (30 g) is added to a stirred mixture of HNO$_3$ (60 ml) and H$_2$SO$_4$ (6 ml) cooled at −15° C.

The reaction mixture, warmed at room temperature, is poured in ice (450 g) and the crystalline precipitate is separated by filtration affording from ethylether 21.7 g of 4-(m-nitrobenzoyl)-butanoic acid m.p. 135°–137° C. A solution of this compound in acetic acid (500 ml) and acetic anhydride (30 ml) is hydrogenated at 65° C. in the presence of 10% Palladium on charcoal (3 g). The catalyst is filtered out; the eluate is concentrated at 50 ml in vacuum and then diluted with water (150 ml). The precipitate is separated by filtration and crystallized from aqueous ethanol yielding 5-(m-acetylaminophenyl)pentanoic acid (16.8 g) m.p. 137°–138° C.

This compound is added to a polyphosphoric acid (85% $P_2O_5$, 110 ml) solution warmed at 100° C. The mixture is kept for 3 hours at this temperature and then poured in ice and water (500 g). The aqueous phase is extracted with methylenedichloride; the organic extracts are collected, washed to neutrality with 5% aqueous $NaHCO_3$ solution, dried on $Na_2SO_4$ and evaporated to dryness. The residue is crystallized from ethanol to yield 7-acetylamino-benzocycloheptan-1-one (8.23 g) m.p. 115°–116° C.

I.R.=3300, 1650, 1600 cm$^{-1}$. H-NMR (CDCl$_3$/TMS): 7.2 (m, 3H, Ar); 2.2–3.0 (m, 8H); 1.8 (s, 3H, CH$_3$CO—).

Glyoxylic acid is prepared "in situ" by addition of a cooled solution of tartaric acid (9.4 g) in water (27 ml) to a stirred solution of periodic acid in water (72 ml) from NaIO$_4$ (9.8 g) and H$_2$SO$_4$ (1.25 ml), cooled at 0°–2° C. 7-Acetylamino-benzocycloheptan-1-one (6.5 g), 2.75N aqueous NaOH (170 ml) and ethanol (160 ml) are then added to this mixture keeping the reaction temperature at about 20°–24° C. for 16 hours.

After further dilution with water (250 ml), the mixture is washed with ethylether for removing neutral unreacted material. The aqueous phase is acidified with 4N H$_2$SO$_4$ to complete precipitation of a yellow material which is separated by filtration. This material is crystallized from ethanol to give 7-acetylamino-1-oxo-benzocycloheptan-2-yliden-acetic acid (6.15 g) m.p. 240°–243° C. I.R. 3300, 1720, 1650 and 1600 cm$^{-1}$.

H-NMR (DMSO-d$_6$/TMS): 10.2 (s, 1H, NH); 7.4–7.6 (m, 3H, Ar); 6.6 (s, 1H,

2.4–3.6 (m, 6H); 2.0 (s, 3H, CH$_3$CO).

Zinc dust (5.3 g) is added in portions to a stirred suspension of the 7-acetylamino-1-oxo-benzocyclohepten-2-yl-acetic acid (6 g) in 80% aqueous acetic acid (70 ml), warmed at 100° C.; the stirring is continued for 1 hour. The inorganic materials are removed by filtration and washed with warm 80% aqueous acetic acid (70 ml).The eluates are collected and acetic acid is distilled off under vacuum. The residual aqueous phase is extracted with ethyl ether, the combined extracts are dried on Na$_2$SO$_4$ and the solvents are evaporated. The crude material is triturated with hexane-ethyl ether to give 7-acetylamino-1-oxo-benzocycloheptan-2-yl-acetic acid (5.1 g) m.p. 198° C.

Furthermore, hydrolysis with 6N aqueous HCl at reflux temperature, gives 7-amino-1-oxo-benzocycloheptan-2-yl-acetic acid (4.2 g).

EXAMPLE 13

Using 3-benzoyl-propionic acid instead of the 4-benzoyl-butanoic acid in the procedure of the Example 12 the following intermediates are obtained:
3-(m-nitrobenzoyl)propionic acid;
3-(m-acetylaminophenyl)butanoic acid;
6-acetylamino-1-oxo-1,2,3,4-tetrahydro-naphthalene.

EXAMPLE 14

A solution of malonic acid monoethylester (19.8 g) under N$_2$ atmosphere in dry tetrahydrofurane (50 ml) is added dropwise to a stirred suspension of magnesium ethoxide (8.58 g) in dry tetrahydrofurane. (40 ml) and the stirring is continued until complete solution of the reagent.

Separately, a solution of m-nitrobenzoic acid (16.7 g) in dry THF (40 ml) is added dropwise to a stirred solution of carbonyldiimidazole (16.8 g) in dry THF (40 ml), cooled to 0°–5° C. in a period of 20 minutes. The obtained m-nitrobenzoylimidazolide solution is then added to the stirred solution of the magnesium-monomalonic ethylester complex in ten minutes and the stirring is continued for 1 hours.

The reaction mixture is then poured in 10% aqueous NaH$_2$PO$_4$ (400 ml) and the precipitate is separated by filtration to give m-nitrobenzoylacetic acid ethyl ester (12.2 g).

A solution of this compound in acetic acid (250 ml) and trifluoroacetic anhydride (12 ml), according to the procedure of the Example 12, is hydrogenated to give 3-(m-trifluoroacetylamino-phenyl)-propionic acid and then cyclized with polyphosphoric acid to give 5-trifluoroacetylamino-indan-1-one. one.

EXAMPLE 15

Using 5-trifluoroacetylamino-indan-1-one in the procedure of the Examples 12 and 1 the following compounds are obtained:
5-trifluoroacetylamino-1-oxo-indan-2-yliden-acetic acid;
5-trifluoroacetylamino-1-oxo-indan-2-yl-acetic acid;
dl-7-trifluoroacetylamino-4,4a-dihydro-5H-indeno-[1,2-c]-pyridazin-3-one, m.p. 234° C., which is hydrolized with 1N H$_2$SO$_4$ to give dl-7-amino-4,4a-dihydro-5H-indeno[1,2-c]-pyridazin-3-one.

EXAMPLE 16

A solution of (R)-(+)-1-phenylethylamine (2.69 g) in ethanol (30 ml) is added to a stirred suspension of dl-6-acetylamino-1-oxo-1,2,3,4-tetrahydro-naphth-2-yl-acetic acid (5.8 g) in ethanol (90 ml). The mixture is heated at 60° C. to obtain complete solution of the reagents then it is spontaneously cooled to room temperature.

The feeble pink crystalline material (4.6 g) which is separated from the solution is filtered and crystallized two times from ethanol to give (+)-6-acetylamino-1-oxo-1,2,3,4-tetrahydro-naphth-2-yl-acetic acid-(R)-(+)-1-phenylethyl-ammonium salt, m.p. 195° C. (2.8 g).

The salt is dissolved in water after treatment with 2N hydrochloric acid the (+)-6-acetylamino-1-oxo-1,2,3,4-tetrahydro-naphth-2-yl-acetic acid $[\alpha]_D^{20} = +23.2°$ (DMSO) m.p. 195° C. is collected by filtration.

Using in this procedure the (S)-(−)-1-phenylethylamine, ethylamine, the (−)-6-acetylamino-1-oxo-1,2,3,4-tetrahydro-naphth-2-yl-acetic acid $[\alpha]_D^{20} = -22.75°$(DMSO), m.p. 193° C. is obtained.

EXAMPLE 17

A suspension of (1R,2S)-(−)-ephedrine (5.36 g) and of dl-(5-acetylamino-1-oxo-indan-2-yl) acetic acid (8 g) in ethanol (24 ml) is heated at the reflux temperature to obtain complete solution of the reagents.

After spontaneous cooling at room temperature, the crystalline material which is separated from the solution, is filtered (6.09 g) and crystalline three times from ethanol to give pure (−)-5-acetylamino-1-oxoindan-2-yl)-acetic acid (1R,2S)-(−)-ephedrinium salt, m.p. 160°-162° C.

The salt is dissolved in water and after treatment with 2N $H_2SO_4$, the (−)-(1-oxo-5-acetylamino-indan-2-yl)-acetic acid ($[\alpha]_D = -31.1$ (DMSO), m.p. 190°-192° C.) is obtained. Using (1S,2R)-(+)-ephedrine in this procedure, the (+)-(1-oxo-5-acetylamino-indan-2-yl)-acetic acid ($[\alpha]_D = +32$ (DMSO), m.p. 191°-192° C. is also prepared.

EXAMPLE 18

90% Hydrazine hydrate (0.32 ml) is added to a solution of (+)-6-acetylamino-1-oxo-1,2,3,4-tetrahydronaphth-2-yl-acetic acid-(R)-(+)-1-phenylethyl ammonium salt (1.1 g) in 50:50-ethanol-water and the mixture is heated at the reflux temperature for 2 hours.

After cooling at room temperature, the crystalline precipitate is filtered to yield 0.72 g of (−)-8-acetylamino-4,4a,5,6-tetrahydro-benzo[h]-cinnolin-3-one, m.p. 283°-288° C.; $[\alpha]_D^{20} = -153°$ (DMSO); $DMSO.d_6$-TMS δ11.4 (S, 1H, =N—NH).

In a similar way, starting from the (Z)-(1-oxo-5-acetylamino-indan-2-yl)-acetic acid-(−)-ephedrinium salt, the (−)-7-acetylamino-4,4a-dihydro-5H-indeno-[1,2-c]-pyridazin-3-one, m.p. 307° C., $[\alpha]_D = -93°$ (DMSO) is obtained.

EXAMPLE 19

Using in the procedure of the examples 4 and 5 the optically active acids:
6-acetylamino-1-oxo-1,2,3,4-tetrahydro-naphth-2-yl-acetic acid
(5-acetylamino-1-oxo-indan-2-yl)-acetic acid
(7-acetylamino-1-oxo-benzocycloheptan-2-yl)-acetic acid
which are prepared in accordance with the procedure of the examples 16 and 17, the following compounds are obtained:
(−)-8-acetylamino-4,4a,5,6-tetrahydro-benzo[h]-cinnolin-3-one
(+)-(8-acetylamino-4,4a,5,6-tetrahydro)-benzo-[h]-cinnolin-3-one, m.p. 284°-285° C., $[\alpha]_D = +158°$ (DMSO);
(−)-7-acetylamino-4,4a-dihydro-5H-indeno-[1,2-c]-pyridazin-3-one
(+)-7-acetylamino-4,4a-dihydro-5H-indeno-[1,2-c]-pyridazin-3-one, m.p. 308°-309° C.; $[\alpha]_D = +92°$ (DMSO);
(−)-9-acetylamino-2,4,4a,5,6,7-hexahydro-3H-benzo-[6,7]-cyclohepten-[1,2-c]-pyridazin-3-one, m.p. 255°-256° C.
(+)-9-acetylamino-2,4,4a,5,6,7-hexahydro-3H-benzo-[6,7]-cyclohepten-[1,2-c]-pyridazin-3-one, m.p. 252°-253° C.

The dextro rotatory antipodes are more active than the levorotatory ones in all the pharmacological testing procedures.

We claim:
1. A compound of formula I

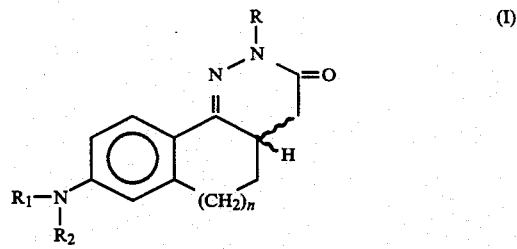

wherein:
n is zero or an integer of 1 to 2;
R is hydrogen, $C_1$-$C_6$ lower alkyl, —$CH_2$—CH=$CH_2$, —$CH_2$—C≡CH or $(CH_2)_m$—$C_6H_5$ where m is zero or an integer of 1 to 3;
$R_1$ and $R_2$ is selected from the group consisting of
(a) $R_3$—CO— wherein $R_3$ is selected from the group consisting of a $C_1$-$C_{16}$ branched or unbranched alkyl chain which may be substituted by hydroxy, amino, halogen, thiol, or free or esterified carboxy group; a heterocyclic ring wherein $R_3$CO is the acyl part of a carboxylic acid $R_3CO_2H$ selected from the group consisting of nicotinic, isonicotinic, pyrazol-3-carboxylic, isoxazol-3-carboxylic, isoxazol-5-carboxylic, 2-thiophencarboxylic and 2-furylcarboxylic acids; an aromatic ring wherein $R_3$CO is the acyl part of a carboxylic acid $R_3CO_2H$ selected from the group consisting of benzoic, toluic, 3,4,5-trimethoxybenzoic, p-hydroxy-3,5-dimethoxybenzoic, p-flurobenzoic, p-chlorobenzoic, p-aminobenzoic, salicyclic, and hydroxybenzoic acid; a $C_3$-$C_7$ cycloaliphatic ring; a $C_4$-$C_{15}$ cycloaliphatic alkyl group; phenyl lower alkyl or phenoxy lower alkyl; moieties wherein $R_3$CO is the acyl part of a carboxylic acid $R_3CO_2H$ selected from the group consisting of 1-imidazolylacetic, 2-furylpropionic, 2-tetrahydrofurylpropionic, cinnamic, 2-fluro-cinnamic, and caffeic acid; a lower $C_1$-$C_6$ alkoxy, benzyloxy or $NHR_6$ group, wherein $R_6$ is hydrogen, $C_1$-$C_6$ lower alkyl or —$CH_2$—$C_6H_5$;
(b) $R_4SO_2$—, wherein $R_4$ is $CH_3$, $C_2H_5$, phenyl or p-methylphenyl; and the other of $R_1$ and $R_2$ is selected from the group consisting of hydrogen, $C_1$-$C_6$ lower alkyl, $(CH_2)_m$—$C_6H_5$, $(CH_2)_m$—$C_6H_{11}$, $(CH_2)_m$—$C_5H_9$ where m is zero or an integer of 1 to 3, —$CH_2$—CH=$CH_2$, —$CH_2$—C≡CH, $R_3$—CO—, and $R_4SO_2$—
and racemic or optically active enantiomers;
and pharmaceutically acceptable salts thereof.
2. A compound selected from the group consisting of:

4,4a-dihydro-5H-indeno[1,2-c]pyridazin-3-one-7-amino;
4,4a-dihydro-5H-indeno[1,2-c]pyridazin-3-one-7-formamide;
4,4a-dihydro-5H-indeno[1,2-c]pyridazin-3-one-7-acetamide;
4,4a-dihydro-5H-indeno[1,2-c]pyridazin-3-one-7-benzamide;
4,4a-dihydro-5H-indeno[1,2-c]pyridazin-3-one-7-(3′,4′,5′-trimethoxy)-benzamide;
4,4a-dihydro-5H-indeno[1,2-c]pyridazin-3-one-7-nicotinyl-amide;
4,4a,5,6-tetrahydro-2H-benzo(h)cinnolin-3-one-8-acetamide;
4,4a,5,6-tetrahydro-2H-benzo(h)-cinnolin-3-one-8-2′-chloroacetamide;

2-n-butyl-4,4a,5,6-tetrahydro-2H-benzo(h)cinnolin-3-one-8-amino;

2-n-butyl-2,4,4a,5,6,7-hexahydro-3H-[6,7]-cyclohepten-[1,2-c]-pyridazin-3-one-8-amino;

2-n-butyl-2,4,4a,5,6,7-hexahydro-3H-[6,7]-cyclohepten-[1,2-c]-pyridazin-3-one-8-benzamide;

2,4,4a5,6,7-hexahydro-3H-benzo-[6,7]-cyclohepten[1,2-c]-pyridazin-3-one-8-amino;

2,4,4a,5,6,7-hexahydro-3H-benzo-[6,7]-cyclohepten[1,2-c]-pyridazin-3-one-8-acetamide;

2,4,4a,5,6,7-hexahydro-3H-benzo-[6,7]-cyclohepten[1,2-c]-pyridazin-3-one-8-benzamide;

and their non toxic salts.

3. Compound of claim 1, wherein n is zero.
4. Compound of claim 1, wherein n is 1.
5. Compound of claim 1, wherein n is 2.
6. Compound of any one of claim 3, 4 or 5 wherein $R_1$ or $R_2$ are both hydrogen, or $R_1$ is hydrogen and $R_2$ is $R_3$—CO—, wherein $R_3$ is substituted or unsubstituted alkyl.
7. An antihypertensive, vasodilating, anti-aggregating, anti-thrombotic or cytoprotective pharmaceutical or veterinary composition in a form suitable for administration by intravenous, subcutaneous, intramuscular, rectal or implant routes, said composition comprising a pharmaceutically and/or veterinarily acceptable carrier and/or diluent and an antihypertensively, vasodilatingly, anti-aggregatingly, anti-thrombotically or cytoprotectively effective amount of a compound of formula I

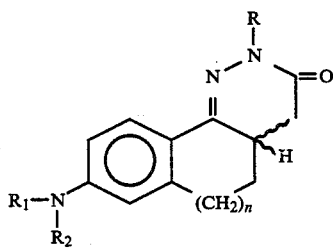

wherein;
n is zero or an integer of 1 to 2
R is hydrogen, $C_1$-$C_6$ lower alkyl, —CH$_2$—CH=CH$_2$, —CH$_2$—C≡CH and $(CH_2)_m$—$C_6H_5$ where m is zero or an integer of 1 to 3;
at least one of $R_1$ and $R_2$ is selected from the group consisting of
(a) $R_3$—CO— wherein $R_3$ is selected from the group consisting of a $C_1$-$C_{16}$ branched or unbranched alkyl chain which may be substituted by hydroxy, amino, halogen, thiol, or free or esterified carboxy group; a heterocyclic ring wherein $R_3$CO is the acyl part of a carboxylic acid $R_3CO_2H$ selected from the group consisting of nictoinic, isonicotinic, pyrazol-3-carboxylic, isoxazol-3-carboxylic, isoxazol-5-carboxylic, 2-thiophencarboxylic and 2-furylcarboxylic acids; an aromatic ring wherein $R_3$CO is the acyl part of a carboxylic acid $R_3CO_2H$ selected from the group consisting of benzoic, toluic, 3,4,5-trimethoxybenzoic, p-hydroxy-3,5-dimethoxybenzoic, p-fluorobenzoic, p-chlorobenzoic, p-aminobenzoic, salicyclic, and p-hydroxybenzoic acid; a $C_3$-$C_7$ cycloaliphatic ring; a $C_4$-$C_{15}$ cycloaliphatic alkyl group; phenyl lower alkyl or phenoxy lower alkyl; moieties wherein $R_3$CO is the acyl part of a carboxylic acid $R_3CO_2H$ selected from the group consisting of 1-imidazolylacetic, 2-furylpropionic, 2-tetrahydrofurylpropionic, cinnamic, 2-fluoro-cinnamic, and caffeic acid; a lower $C_1$-$C_6$ alkoxy, benzyloxy or $NHR_6$ group, wherein $R_6$ is hydrogen, $C_1$-$C_6$ lower alkyl or —$CH_2$—$C_6H_5$;
(b) $R_4SO_2$—, wherein $R_4$ is $CH_3$, $C_2H_5$, phenyl or p-methylphenyl; and the other of $R_1$ and $R_2$ is selected from the group consisting of hydrogen, $C_1$-$C_6$ lower alkyl, $(CH_2)_m$—$C_6H_5$, $(CH_2)_m$—$C_6H_{11}$, $(CH_2)_m$—$C_5H_9$ where m is zero or an integer of 1 to 3, —$CH_2$—CH=$CH_2$, —$CH_2$—C≡CH, $R_3$—CO—, and $R_4SO_2$—
and racemic or optically active enantiomers;
and pharmaceutically acceptable salts thereof.

* * * * *